(12) United States Patent
Cho et al.

(10) Patent No.: US 12,152,792 B2
(45) Date of Patent: Nov. 26, 2024

(54) CLEAN NEGATIVE PRESSURE HOSPITAL ROOM SYSTEM USING COMPRESSOR AND TURBINE

(71) Applicant: KOREA INSTITUTE OF ENERGY RESEARCH, Daejeon (KR)

(72) Inventors: Jongjae Cho, Sejong-si (KR); Hyungki Shin, Daejeon (KR); Beomjoon Lee, Sejong-si (KR); Gyunchul Hur, Sejong-si (KR); Junhyun Cho, Daejeon (KR); Bongsu Choi, Daejeon (KR); Chulwoo Roh, Sejong-si (KR); Young-Jin Baik, Daejeon (KR); Ho-sang Ra, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 538 days.

(21) Appl. No.: 17/458,563

(22) Filed: Aug. 27, 2021

(65) Prior Publication Data
US 2022/0065466 A1 Mar. 3, 2022

(30) Foreign Application Priority Data
Aug. 28, 2020 (KR) .......................... 10-2020-0109255

(51) Int. Cl.
*F24F 1/0041* (2019.01)
*A61L 2/02* (2006.01)
(Continued)

(52) U.S. Cl.
CPC ............ *F24F 1/0041* (2019.02); *A61L 2/022* (2013.01); *F24F 1/00073* (2019.02);
(Continued)

(58) Field of Classification Search
CPC ........ F24F 1/0041; F24F 1/00073; F24F 8/22; F24F 2012/007; F24F 3/001; F24F 7/06;
(Continued)

(56) References Cited

U.S. PATENT DOCUMENTS 2,293,557 A * 8/1942 Newton ................ F24F 5/0085
62/177
2,730,874 A * 1/1956 Schelp ................. B60H 1/3202
62/88
(Continued)

FOREIGN PATENT DOCUMENTS

CA 3079713 A1 * 10/2021
CN 105299788 A * 2/2016
(Continued)

*Primary Examiner* — Avinash A Savani
*Assistant Examiner* — Frances F. Hamilton
(74) *Attorney, Agent, or Firm* — CANTOR COLBURN LLP

(57) ABSTRACT

The present disclosure sucks air in hospital room using a compressor to maintain an inner portion of the hospital room in a negative pressure state, and creates a high-temperature and humid environment by a water spray, the compressor, and a sterilization chamber to kill bacteria or viruses. In addition, the compressor uses power generated by a turbine, and is configured so that heat of air coming out of the compressor is recovered to a suction side of the compressor, such that efficiency of a system may be secured. Further, some of clean air generated while passing through the sterilization chamber may be directly supplied again to the hospital room through a bypass means.

8 Claims, 4 Drawing Sheets

(51) Int. Cl.
*F24F 1/0007* (2019.01)
*F24F 5/00* (2006.01)
*F24F 8/22* (2021.01)
*F24F 12/00* (2006.01)
*B01D 35/02* (2006.01)

(52) U.S. Cl.
CPC .............. *F24F 5/0085* (2013.01); *F24F 8/22* (2021.01); *B01D 35/02* (2013.01); *F24F 2012/007* (2013.01)

(58) Field of Classification Search
CPC .... F24F 5/0085; A61L 2/022; A61L 2202/16; A61L 2209/14; A61L 9/20; B01D 35/02; A61G 10/023; A61G 10/005
USPC .......................................................... 454/187
See application file for complete search history.

(56) References Cited

U.S. PATENT DOCUMENTS

| | | | | | |
|---|---|---|---|---|---|
| 3,222,883 | A | * | 12/1965 | Glaspie | F24F 3/153 62/93 |
| 3,261,659 | A | * | 7/1966 | Schwichtenberg | F24F 8/95 95/271 |
| 3,966,407 | A | * | 6/1976 | Zuckerberg | F24F 8/20 422/4 |
| 4,732,579 | A | * | 3/1988 | Veltman | B01D 53/04 96/136 |
| 4,769,051 | A | * | 9/1988 | Defrancesco | F24F 8/108 96/144 |
| 4,793,832 | A | * | 12/1988 | Veltman | B01D 53/04 96/112 |
| 5,151,022 | A | * | 9/1992 | Emerson | B60H 3/06 62/401 |
| H1189 | H | * | 5/1993 | Kirts | 423/245.3 |
| 6,099,617 | A | * | 8/2000 | Bennett | B64D 13/06 95/143 |
| 6,312,328 | B1 | * | 11/2001 | Nakajima | B01D 53/75 414/940 |
| 6,401,473 | B1 | * | 6/2002 | Ng | B64D 13/06 62/401 |
| 7,125,439 | B2 | * | 10/2006 | Bennett | B01D 53/047 96/121 |
| 9,005,530 | B2 | * | 4/2015 | Nevin | F04B 41/02 422/121 |
| 9,211,954 | B2 | * | 12/2015 | Barkowsky | B64D 13/06 |
| 10,994,034 | B1 | * | 5/2021 | Leavitt | A61L 2/26 |
| 2008/0292494 | A1 | * | 11/2008 | Garvey | A61L 9/16 422/4 |
| 2011/0185752 | A1 | * | 8/2011 | Holzner | F24F 3/147 62/412 |
| 2019/0009912 | A1 | * | 1/2019 | Matsui | B64D 13/02 |
| 2021/0269164 | A1 | * | 9/2021 | Sun | A61L 9/16 |

FOREIGN PATENT DOCUMENTS

| | | | | |
|---|---|---|---|---|
| CN | 106839142 A | * | 6/2017 | |
| GB | 2447948 A | * | 10/2008 | ............ F24F 5/0071 |
| JP | 2018021752 A | * | 2/2018 | |
| KR | 20-0406536 Y1 | | 1/2006 | |

* cited by examiner

CLEAN NEGATIVE PRESSURE HOSPITAL ROOM SYSTEM USING COMPRESSOR AND TURBINE

CROSS-REFERENCE TO RELATED APPLICATIONS

This application claims priority under 35 U.S.C. § 119 to Korean Patent Application No. 10-2020-0109255, filed on Aug. 28, 2020, in the Korean Intellectual Property Office, the disclosure of which is incorporated herein by reference in its entirety.

TECHNICAL FIELD

The following disclosure relates to a clean air conditioning system using a compressor and a turbine that may be applied to a negative pressure hospital room or the like.

BACKGROUND

In general, a negative pressure hospital room refers to a special isolation hospital room for blocking air including germs and viruses from spreading outward by artificially dropping air pressure inside the hospital room. That is, the negative pressure hospital room is a space designed so that air outside the hospital room may enter the hospital room, but air inside the hospital room may not go out of the hospital room, due to an air pressure difference. The negative pressure hospital room allows air with which viruses discharged through patient's breathing or the like are mixed not to go out of the hospital room, and allows the viruses to be caught through a purification facility installed on the ceiling or the like of the hospital room, such that leakage of the viruses to the outside may be prevented. Therefore, the negative pressure hospital room is used as a hospital room for accommodating and treating a patient separately from the outside and general patients in order to prevent the spread of an infectious disease.

Recently, as the seriousness of a pandemic of the infectious disease has risen, the need for isolation treatment of virus patients has increased, such that an interest in the negative pressure hospital room has increased.

RELATED ART DOCUMENT

Patent Document

Korean Utility Model No. 20-0406536

SUMMARY

An embodiment of the present disclosure is directed to providing a clean air conditioning system using a compressor and a turbine capable of purifying, cooling, and heating air in a hospital room while maintaining an inner portion of the hospital room in a negative pressure state.

In one general aspect, a clean air conditioning system using a compressor includes: an exhaust chamber exhausting polluted air in a hospital room; an ultraviolet lamp provided in the exhaust chamber and sterilizing the air coming out of the hospital room; a filter provided in the exhaust chamber and filtering the air passing through the ultraviolet lamp; a compressor compressing and discharging the air passing through the filter; a sterilization chamber connected to the compressor to form a space in which the air discharged from the compressor is sterilized while passing therethrough; and a driving turbine driven by the air discharged from the sterilization chamber to generate power and providing the generated power to the compressor.

The clean air conditioning system using a compressor may further include a heat recovery flow passage formed to circulate the air discharged from the compressor to the exhaust chamber through the sterilization chamber and to be connected from the exhaust chamber to the driving turbine.

The clean air conditioning system using a compressor may further include a heat recovery valve installed in the heat recovery flow passage and controlling a flow rate of the circulated air.

The clean air conditioning system using a compressor may further include a heater provided between the sterilization chamber and the hospital room and bypassing some of the air sterilized in the sterilization chamber to supply high-temperature air to the hospital room.

The heater may include: a heat exchanger heating external air with high-temperature clean air coming out of the exhaust chamber of the heat recovery flow passage; a second clean air supply flow passage bypassing some of the clean air before being introduced into the heat exchanger to supply some of the clean air to the hospital room; and a discharge flow passage discharging the clean air from the heat exchanger to the outside.

The clean air conditioning system using a compressor may further include an air conditioner driving the driving turbine and bypassing some of discharged clean air to supply low-temperature air to the hospital room.

The air conditioner may include: a bypass flow passage bypassing some of the clean air from a turbine discharge flow passage discharging the clean air from the driving turbine to the outside; a cooling heat exchanger heat-exchanging the clean air passing through the bypass flow passage with a refrigerant to cool the clean air; and a first clean air supply flow passage bypassing some of the clean air before being introduced into the cooling heat exchanger to supply some of the clean air to the hospital room.

The sterilization chamber may be provided with an ultraviolet lamp.

The sterilization chamber may be provided with a filter.

In another general aspect, a clean air conditioning system using a compressor includes: an exhaust chamber exhausting polluted air in a hospital room; a water spray spraying water into the air passing through the exhaust chamber to raise a humidity of the air; a compressor compressing the air passing through the water spray and discharging high-temperature and humid air; a sterilization chamber connected to the compressor to form a space in which the high-temperature and humid air discharged from the compressor is sterilized while passing therethrough; and a driving turbine driven by the air discharged from the sterilization chamber to generate power and providing the generated power to the compressor.

The clean air conditioning system using a compressor may further include: a heat recovery flow passage connected to a discharge port of the driving turbine and formed to circulate at least some of the air discharged from the driving turbine to the exhaust chamber to transfer heat of the air discharged from the driving turbine to air passing through the exhaust chamber; and a heat recovery valve installed in the heat recovery flow passage and controlling a flow rate of the circulated air.

The clean air conditioning system using a compressor may further include: a bypass means provided between the sterilization chamber and the hospital room and bypassing some of the air sterilized in the sterilization chamber to supply some of the air to the hospital room.

The bypass means may include: a bypass flow passage connected to the sterilization chamber and bypassing clean air that has been sterilized in the sterilization chamber and has not yet been introduced into the driving turbine; a cooling heat exchanger heat-exchanging the clean air passing through the bypass flow passage with a refrigerant to cool the clean air; and a clean air supply flow passage supplying the clean air coming out of the cooling heat exchanger to the hospital room.

The bypass means may further include a bypass valve installed in the bypass flow passage and controlling a flow rate of the bypassed air.

The bypass means may further include a cooling turbine installed in the clean air supply flow passage, driven by the air passing through the clean air supply flow passage, and cool the air.

The bypass means may further include a blower installed in the clean air supply flow passage and pumping the air passing through the clean air supply flow passage to the hospital room.

The clean air conditioning system using a compressor may further include an ultraviolet lamp provided on an upstream side of the water spray in the exhaust chamber and sterilizing the polluted air coming out of the hospital room.

The clean air conditioning system using a compressor may further include a filter provided on an upstream side of the water spray in the exhaust chamber and filtering the polluted air coming out of the hospital room.

The sterilization chamber may include a spiral flow passage so that the high-temperature and humid air discharged from the compressor passes therethrough for a minimum set time or more.

The sterilization chamber may be provided with an ultraviolet lamp.

The sterilization chamber may be provided with a filter.

In still another general aspect, a clean air conditioning system using a compressor includes: an exhaust chamber exhausting polluted air in a hospital room; an ultraviolet lamp provided in the exhaust chamber and sterilizing the air coming out of the hospital room; a filter provided in the exhaust chamber and filtering the air that passing through the ultraviolet lamp; a water spray spraying water into the air passing through the filter to raise a humidity of the air; a compressor compressing the air passing through the water spray and discharging high-temperature and humid air; a sterilization chamber connected to the compressor to form a space in which the high-temperature and humid air discharged from the compressor is sterilized while passing therethrough; a driving turbine driven by the air discharged from the sterilization chamber to generate power and providing the generated power to the compressor; a heat recovery flow passage connected to a discharge port of the driving turbine and formed to circulate at least some of the air discharged from the driving turbine to the water spray to transfer heat of the air discharged from the driving turbine to air passing through the water spray; and a heat recovery valve installed in the heat recovery flow passage and controlling a flow rate of the circulated air.

In still another general aspect, a clean air conditioning system using a compressor includes: an exhaust chamber exhausting polluted air in a hospital room; an ultraviolet lamp provided in the exhaust chamber and sterilizing the air coming out of the hospital room; a filter provided in the exhaust chamber and filtering the air that passing through the ultraviolet lamp; a water spray spraying water into the air passing through the filter to raise a humidity of the air; a compressor compressing the air passing through the water spray and discharging high-temperature and humid air; a sterilization chamber connected to the compressor to form a space in which the high-temperature and humid air discharged from the compressor is sterilized while passing therethrough; a driving turbine driven by the air discharged from the sterilization chamber to generate power and providing the generated power to the compressor; a heat recovery flow passage connected to a discharge port of the driving turbine and formed to circulate at least some of the air discharged from the driving turbine to the water spray to transfer heat of the air discharged from the driving turbine to air passing through the water spray; a heat recovery valve installed in the heat recovery flow passage and controlling a flow rate of the circulated air; and a bypass means provided between the sterilization chamber and the hospital room and bypassing some of the air sterilized in the sterilization chamber to supply some of the air to the hospital room, wherein the bypass means includes: a bypass flow passage connected to the sterilization chamber and bypassing clean air that has been sterilized in the sterilization chamber and has not yet been introduced into the driving turbine; a bypass valve installed in the bypass flow passage and controlling a flow rate of the bypassed air; a cooling heat exchanger heat-exchanging the clean air passing through the bypass flow passage with a refrigerant to cool the clean air; a clean air supply flow passage supplying the clean air cooled while passing through the cooling heat exchanger to the hospital room; and a cooling turbine installed in the clean air supply flow passage, driven by the air passing through the clean air supply flow passage to generate power, cooling the air, and providing the generated power to the compressor

DETAILED DESCRIPTION OF EMBODIMENTS

Hereinafter, embodiments of the present disclosure will be described with reference to the accompanying drawings.

Figure 1:
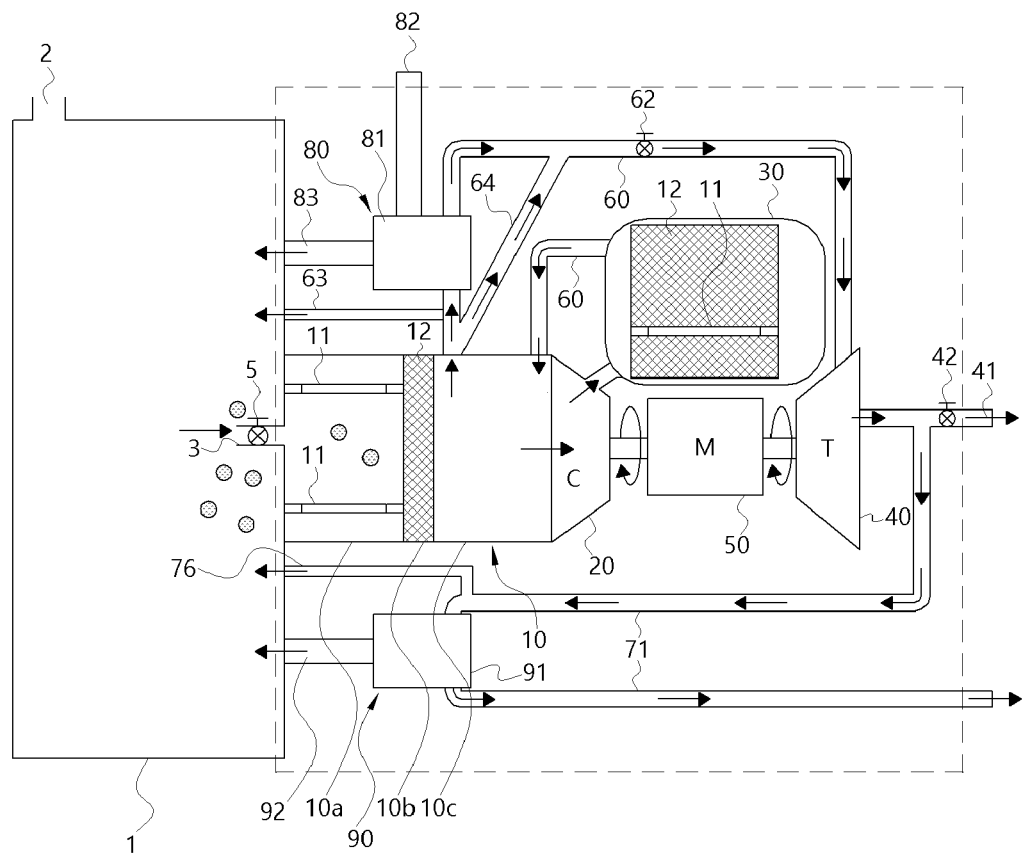
FIG. 1 is a schematic view illustrating a configuration of a clean air conditioning system using a compressor and a turbine according to an embodiment of the present disclosure.

FIG. 1 is a schematic view illustrating a configuration of a clean air conditioning system using a compressor and a turbine according to an embodiment of the present disclosure.

Referring to FIG. 1, a clean air conditioning system using a compressor and a turbine according to an embodiment of the present disclosure includes an exhaust chamber 10, ultraviolet lamps 11, a filter 12, a compressor 20, a sterilization chamber 30, a driving turbine 40, a motor 50, a heat recovery flow passage 60, a bypass flow passage 71, a heater 80, and an air conditioner 90.

The exhaust chamber 10 is connected to a hospital room 1 to exhaust polluted air in the hospital room 1.

The hospital room 1 is provided with a suction port 2 through which external air is sucked, an exhaust port 3 connected to the exhaust chamber 10 to exhaust the polluted air in the hospital room, and a first clean air supply flow passage 76 which is connected to the bypass flow passage 71 and through which clean air is supplied from the bypass flow passage 71.

An exhaust valve 5 controlling an exhaust amount of the polluted air in the hospital room is installed at the exhaust port 3.

It is described by way of example that the exhaust chamber 10 is partitioned into first, second, and third exhaust spaces 10a, 10b, and 10c. The first, second, and third exhaust spaces 10a, 10b, and 10c are sequentially disposed in an exhaust direction, and are disposed to communicate with each other.

The ultraviolet lamps 11 are installed inside the first exhaust space 10a. The filter 12 is installed inside the second exhaust space 10b.

A plurality of ultraviolet lamps 11 are installed to be spaced apart from each other by a predetermined interval, and primarily kill bacteria or viruses included in the polluted air passing through the exhaust chamber 10.

As the filter 12, an antibacterial filter, an antiviral filter, or the like, that removes dust, foreign substances, and the like, included in the air passing through the ultraviolet lamp 11, and also filters bacteria, viruses, or the like, may be used.

In the present embodiment, it is described by way of example that the ultraviolet lamp 11 and the filter 12 are sequentially installed in the exhaust direction inside the exhaust chamber 10. However, the present disclosure is not limited thereto, and an installation order of the ultraviolet lamp 11 and the filter 12 inside the exhaust chamber 10 may be changed or only one of the ultraviolet lamp 11 and the filter 12 may be installed inside the exhaust chamber 10.

The compressor 20 compresses the air passing through the exhaust chamber 10 and discharges high-temperature air. The compressor 20 is connected to and driven by a rotation shaft 51 of the motor 50.

The compressor 20 and the driving turbine 40 are connected to each other by the rotation shaft 51 of the motor 50, such that power generated by the driving turbine 40 is provided to the compressor 20 through the rotation shaft 51.

The sterilization chamber 30 is connected to a discharge side of the compressor 20 by the heat recovery flow passage 60. The heat recovery flow passage 60 is circulated again to the exhaust chamber 10 through the sterilization chamber 30.

The sterilization chamber 30 is a flow passage formed so that the air coming out of the compressor 20 is sterilized while passing therethrough at a high-temperature state for a minimum set time or more. The minimum set time is set as a minimum exposure time in which bacteria or viruses may be exposed to and killed in a high-temperature environment. A shape, a length, and a cross-sectional area of the sterilization chamber 30 may be set differently according to the minimum exposure time.

At least one of a filter 12 for filtering pollutants in the air passing through the sterilization chamber 30 and an ultraviolet lamp 11 for killing bacteria or viruses included in the air passing through the sterilization chamber 30 may be installed in the sterilization chamber 30. The filter 12 and the ultraviolet lamp 11 may be detachably inserted into the sterilization chamber 30.

The driving turbine 40 is driven by the air coming out of the heat recovery flow passage 60 circulated from the sterilization chamber 30 through the exhaust chamber 10 to generate power, and provides the generated power to the compressor 20.

The driving turbine 40 generates power by clean air circulated through the heat recovery flow passage 60 and entering the driving turbine 40. Then, the clean air is discharged to the outside by a turbine discharge flow passage 41. A turbine discharge valve 42 for controlling a flow rate of clean air discharged to the outside is installed in the turbine discharge flow passage 41.

The heat recovery flow passage 60 connects a discharge port of the driving turbine 40 and the sterilization chamber 30 to each other, and again connects the sterilization chamber 30 and the exhaust chamber 10 to each other. That is, the heat recovery flow passage 60 is connected so that the air may be circulated from the exhaust chamber 10 to the sterilization chamber 30 and from the sterilization chamber 30 to the exhaust chamber 10 again.

The heat recovery flow passage 60 and the third exhaust space 10c do not communicate with each other, and are formed as independent flow passages, such that only heat exchange is performed and air is not mixed between the heat recovery flow passage 60 and the third exhaust space 10c.

A heat recovery valve 62 is installed in the heat recovery flow passage 60. The heat recovery valve 62 controls a flow rate of the air circulated through the heat recovery flow passage 60.

Some of the clean air circulated through the heat recovery flow passage 60 is supplied to the hospital room 1 as high-temperature air through the heater 80. The heater 80 is provided between the sterilization chamber 30 and the hospital room 1, and bypasses some of the air sterilized in the sterilization chamber 30 to supply the high-temperature air to the hospital room 1.

The heater 80 includes a heat exchanger 81 heating external air with high-temperature clean air coming out of the exhaust chamber 10 of the heat recovery flow passage 60. The heat exchanger 81 heats the external air with some of the circulated clean air to generate high-temperature heating air. The heat exchanger 81 supplies the high-temperature heating air to the hospital room 1 through a heating supply flow passage 83.

A second clean air supply flow passage 63 for supplying clean air to the hospital room 1 is connected to the heat recovery flow passage 60 connected to the exhaust chamber 10 in a direction in which the air comes out of the exhaust chamber 10. Some of the clean air before being introduced into the heat exchanger 81 is bypassed through the second clean air supply flow passage 63 and supplied to the hospital room 1.

The heater 80 is provided with a discharge flow passage 82 connected to the heat exchanger 81 and discharging the clean air from the heat exchanger to the outside. The discharge flow passage 82 is for discharging the high-temperature clean air that is not supplied to the hospital room 1 to the outside. In the summer when heating is not required, the high-temperature clean air does not need to be supplied to the hospital room 1, and will thus be exhausted through the discharge flow passage 82.

In addition, the heat recovery flow passage 60 may be provided with a direct flow passage 64 connected in a direction toward the turbine discharge flow passage 41 without passing through the heat exchanger 81.

Some of the clean air discharged from the heat recovery flow passage 60 to the turbine discharge flow passage 41 through the turbine 40 is supplied to the hospital room 1 as low-temperature air through an air conditioner 90. The air conditioner 90 bypasses some of the air sterilized in the sterilization chamber 30 to supply the low-temperature air to the hospital room 1.

The turbine discharge flow passage 41 is connected to the air conditioner 90 by the bypass flow passage 71 to allow some of the clean air discharged to the outside to flow to the air conditioner 90.

The air conditioner 90 is provided with a cooling heat exchanger 91 heat-exchanging the clean air passing through the bypass flow passage 71 with a refrigerant to cool the clean air. The cooling heat exchanger 91 cools some of the clean air discharged to the outside to generate cooling air. The cooling heat exchanger 91 supplies the cooing air to the hospital room 1 through a cooling supply flow passage 92.

The first clean air supply flow passage 76 for supplying the clean air to the hospital room 1 is connected to the bypass flow passage 71. Some of the clean air before being introduced into the cooling heat exchanger 91 is bypassed and supplied to the hospital room 1 through the first clean air supply flow passage 76.

Figure 2:
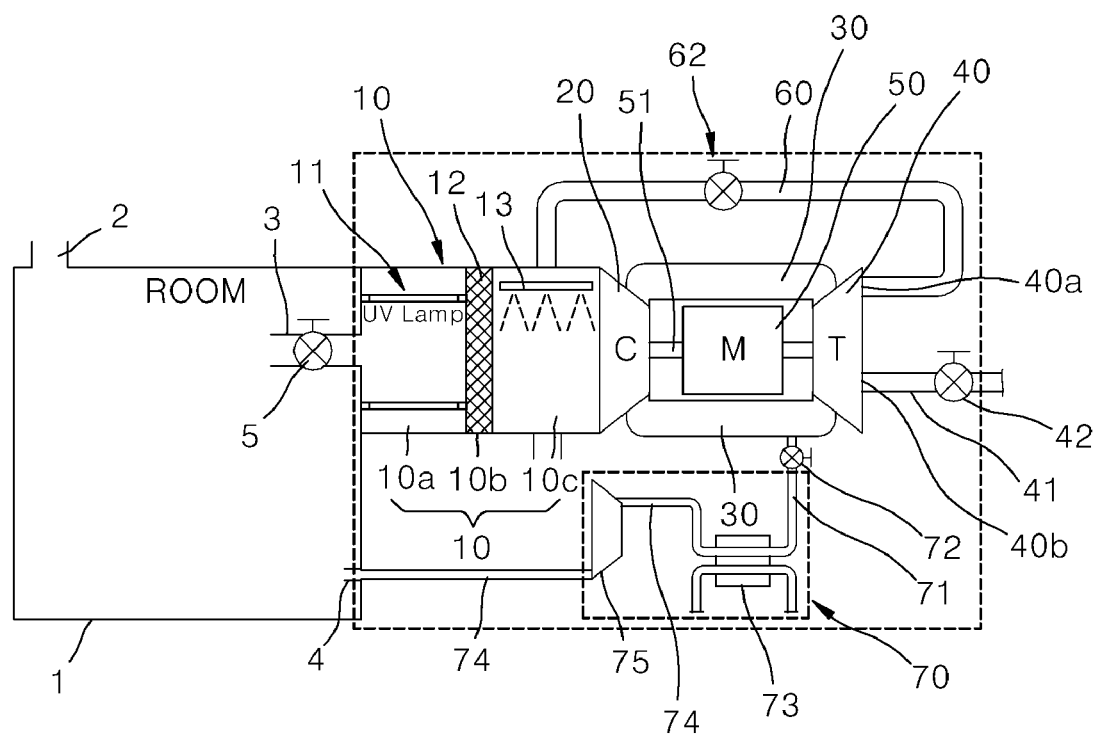
FIG. 2 is a schematic view illustrating a configuration of a clean air conditioning system using a compressor and a turbine according to another embodiment of the present disclosure.

FIG. 2 is a schematic view illustrating a configuration of a clean air conditioning system using a compressor and a turbine according to another embodiment of the present disclosure.

Referring to FIG. 2, a clean air conditioning system using a compressor and a turbine according to another embodiment of the present disclosure includes an exhaust chamber 10, ultraviolet lamps 11, a filter 12, a water spray 13, a compressor 20, a sterilization chamber 30, a driving turbine 40, a motor 50, a heat recovery flow passage 60, and a bypass means 70.

The exhaust chamber 10 is a chamber connected to a hospital room 1 to exhaust polluted air in the hospital room 1.

The hospital room 1 is provided with a suction port 2 through which external air is sucked, an exhaust port 3 connected to the exhaust chamber 10 to exhaust the polluted air in the hospital room 1, and a clean air suction port 4 which is connected to the bypass means 70 and through which clean air is sucked from the bypass means 70. In the present embodiment, it is described by way of example that the clean air suction port 4 and the suction port 2 are separately formed, but the present disclosure is not limited thereto, and the clean air suction port 4 and the suction port 2 may also be formed integrally with each other.

An exhaust valve 5 controlling an exhaust amount of the polluted air in the hospital room 1 is installed at the exhaust port 3.

It is described by way of example that the exhaust chamber 10 is partitioned into first, second, and third exhaust spaces 10a, 10b, and 10c. The first, second, and third exhaust spaces 10a, 10b, and 10c are sequentially disposed in an exhaust direction, and are disposed to communicate with each other.

The ultraviolet lamps 11 are installed inside the first exhaust space 10a.

The filter 12 is installed inside the second exhaust space 10b.

The water spray 13 is installed inside the third exhaust space 10c.

A plurality of ultraviolet lamps 11 are installed to be spaced apart from each other by a predetermined interval, and primarily kill bacteria or viruses included in the polluted air passing through the exhaust chamber 10.

As the filter 12, an antibacterial filter, an antiviral filter, or the like, that removes dust, foreign substances, and the like, included in the air passing through the ultraviolet lamp 11, and also filters bacteria, viruses, or the like, may be used.

The water spray 13 is installed inside the exhaust chamber 10 and sprays water to the air passing through the filter 12 to serve to raise humidity of the air.

In the present embodiment, it is described by way of example that the ultraviolet lamp 11, the filter 12, and the water spray 13 are sequentially installed in the exhaust direction inside the exhaust chamber 10. However, the present disclosure is not limited thereto, and an installation order of the ultraviolet lamp 11 and the filter 12 inside the exhaust chamber 10 may be changed or only one of the ultraviolet lamp 11 and the filter 12 may be installed inside the exhaust chamber 10.

The compressor 20 compresses the air passing through the water spray 13 and discharges high-temperature and humid air. The compressor 20 is connected to and driven by a rotation shaft 51 of the motor 50.

The compressor 20 and the driving turbine 40 are connected to each other by the rotation shaft 51 of the motor 50, such that power generated by the driving turbine 40 is provided to the compressor 20 through the rotation shaft 51.

The sterilization chamber 30 connects a discharge side of the compressor 20 and a suction side of the driving turbine 40 to each other to form a space through which the high-temperature and humid air discharged from the compressor 20 passes.

The sterilization chamber 30 is a flow passage formed so that the air coming out of the compressor 20 is sterilized while passing therethrough at a high-temperature and humid state for a minimum set time or more. The minimum set time is set as a minimum exposure time in which bacteria or viruses may be exposed to and killed in a high-temperature and humid environment. A shape, a length, and a cross-sectional area of the sterilization chamber 30 may be set differently according to the minimum exposure time.

At least one of a filter 12 for filtering pollutants in the air passing through the sterilization chamber 30 and an ultraviolet lamp 11 for killing bacteria or viruses included in the air passing through the sterilization chamber 30 may be installed in the sterilization chamber 30. The filter 12 and the ultraviolet lamp 11 may be detachably inserted into the sterilization chamber 30.

The driving turbine 40 is driven by the air coming out of the sterilization chamber 30 to generate power, and provides the generated power to the compressor 20.

The driving turbine 40 is provided with first and second discharge ports 40a and 40b. The heat recovery flow passage 60 is connected to the first discharge port 40a to circulate the air coming out of the driving turbine 40 to the exhaust chamber 10. A turbine discharge flow passage 41 is connected to the second discharge port 40b to discharge the clean air coming out of the driving turbine 40 to the outside. A turbine discharge valve 42 for controlling a flow rate of clean air discharged to the outside is installed in the turbine discharge flow passage 41. However, the present disclosure is not limited thereto, and one discharge port may be formed in the driving turbine 40 and the turbine discharge flow passage 41 and the heat recovery flow passage may be branched from a flow passage connected to the discharge port.

The heat recovery flow passage 60 is a flow passage formed to connect the discharge port of the driving turbine 40 and the exhaust chamber 10 to each other to circulate at least some of the air discharged from the driving turbine 40 to the exhaust chamber 10, thereby transferring heat of the air discharged from the driving turbine 40 to the air passing through the third exhaust space 10c.

The heat recovery flow passage 60 and the third exhaust space 10c do not communicate with each other, and are formed as independent flow passages, such that only heat exchange is performed and air is not mixed between the heat recovery flow passage 60 and the third exhaust space 10c.

A heat recovery valve 62 is installed in the heat recovery flow passage 60. The heat recovery valve 62 controls a flow rate of the air passing through the heat recovery flow passage 60 and then circulated to the third exhaust space 10c.

The bypass means 70 is a means provided between the sterilization chamber 30 and the hospital room 1 and bypassing some of the air sterilized in the sterilization chamber 30 to supply the bypassed air to the hospital room 1.

The bypass means 70 includes a bypass flow passage 71, a bypass valve 72, a cooling heat exchanger 73, a clean air supply flow passage 74, and a cooling turbine 75.

The bypass flow passage 71 is a flow passage connected to a discharge side of the sterilization chamber 30 and formed to bypass the clean air that has been sterilized in the sterilization chamber 30 and has not yet been introduced into the driving turbine 40.

However, the present disclosure is not limited thereto, and the bypass flow passage 71 may also be branched from the heat recovery flow passage 60 or the turbine discharge flow passage 41.

The bypass valve 72 is a valve provided in the bypass flow passage 71, intermittently opening and closing the bypass flow passage 71, and controlling a flow rate of the bypassed clean air.

The cooling heat exchanger 73 is a heat exchanger heat-exchanging the high-temperature clean air passing through the bypass flow passage 71 with a refrigerant to cool the high-temperature clean air. As the refrigerant, external air, a coolant, or the like, may be used.

The clean air supply flow passage 74 is a flow passage formed to supply the clean air coming out of the cooling heat exchanger 73 to the hospital room. The clean air supply flow passage 74 is connected to the clean air suction port 4. However, the present disclosure is not limited thereto, and the clean air supply flow passage 74 may also be connected to the suction port 2.

The cooling turbine 75 is installed in the clean air supply flow passage 74, is driven by the air passing through the clean air supply flow passage 74, and cools the air passing through the clean air supply flow passage 74.

In addition, power generated by the cooling turbine 75 may also be provided to the compressor 20.

In addition, instead of the cooling turbine 75, a blower or a pump may be installed in the clean air supply flow passage 74.

An operation of the clean air conditioning system using a compressor and a turbine according to another embodiment of the present disclosure configured as described above will be described as follows.

Figure 3:
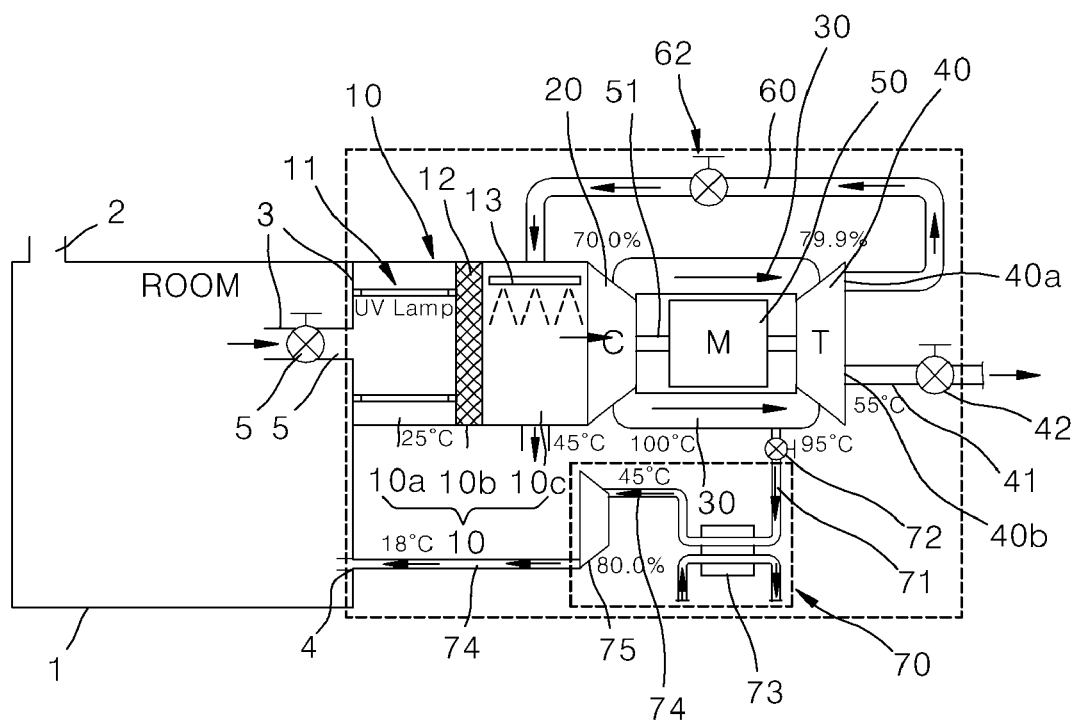
FIG. 3 is a view illustrating an operation of a clean air conditioning system using a compressor and a turbine according to another embodiment of the present disclosure.

Referring to FIG. 3, when the compressor 20 is driven, the polluted air in the hospital room 1 is sucked into the exhaust chamber 10, such that an inner portion of the hospital room 1 is in a negative pressure state.

Bacteria or viruses in the polluted air are primarily killed while the polluted air sucked into the exhaust chamber 10 passes through the ultraviolet lamp 11.

Dust, foreign substances, bacteria, viruses, and the like, in the air are removed while the air passing through the ultraviolet lamp 11 passes through the filter 12.

The air purified while passing through the filter 12 passes through the third exhaust space 10c.

In the third exhaust space 10c, a humidity in the air is raised by the water sprayed from the water spray 13.

In addition, the air passing through the third exhaust space 10c exchanges heat with the high-temperature air circulated through the heat recovery flow passage 60, such that a temperature of the air rises.

For example, when a temperature of the air sucked from the hospital room 1 into the first exhaust space 10a is about 25° C., a temperature of the air before being sucked from the third exhaust space 10c into the compressor 20 is about 45° C. and a humidity in the air is about 70%.

The air coming out of the third exhaust space 10c is compressed by the compressor 20, and then passes through the sterilization chamber 30.

A temperature of the air coming out of the compressor 20 is about 100° C.

Since an inner portion of the sterilization chamber 30 is under a high-temperature and humid condition in which a temperature is about 100° C. and a humidity is about 70, or more, the bacteria or the viruses in the air are completely killed while the air passes through the sterilization chamber 30.

It has been known that COVID-19 or the like may survive for 5 days or more without a host under a condition in which a temperature is 25° C. and a humidity is 50%, but is rapidly killed when a temperature is 56° C. and a humidity is 60% or more.

Therefore, the bacteria or the viruses in the air may be killed while the air passes through the sterilization chamber 30.

The clean air sterilized and purified in the sterilization chamber 30 is introduced into the turbine 40.

The air introduced into the turbine 40 drives the turbine 40, and the power generated by driving the turbine 40 is used to drive the compressor 20 through the motor 50. Therefore, efficiency of the clean air conditioning system may be improved.

Some of the air discharged from the turbine 40 is circulated to the third exhaust space 10c through the heat recovery flow passage 60.

The high-temperature air circulated to the third exhaust space 10c through the heat recovery flow passage 60 exchanges heat with the air passing through the third exhaust space 10c.

The heat of the air circulated through the heat recovery flow passage 60 is transferred to the air passing through the third exhaust space 10c, such that a temperature of the air sucked into the compressor 20 rises.

Therefore, a compression ratio of the compressor 20 is decreased, such that power consumption of the compressor 20 may be decreased.

Meanwhile, some of the air passing through the sterilization chamber 30 is bypassed through the bypass flow passage 71. Some of the air that has sterilized while passing through the sterilization chamber 30 and has not yet been introduced into the driving turbine 40 is bypassed through the bypass flow passage 71.

The air bypassed through the bypass flow passage 71 is primarily cooled in the cooling heat exchanger 73. It is described by way of example that a temperature of the air cooled primarily in the cooling heat exchanger 73 is about 40° C.

The air cooled primarily in the cooling heat exchanger 73 is secondarily cooled by the cooling turbine 75 and then supplied to the hospital room 1. A temperature of the air cooled by the cooling turbine 75 is about 18° C.

In this case, the cooling turbine 75 may also generate power and provide the generated power to the compressor 20.

In this case, a sensor measuring a pollution level may be provided on a discharge port side of the sterilization chamber 30, and when a value measured by the sensor is less than a set pollution level, the bypass valve 72 may be opened to bypass the air sterilized in the sterilization chamber 30.

Therefore, the clean air sterilized in the sterilization chamber 30 may be supplied again to and reused in the hospital room 1.

As described above, the clean air conditioning system using a compressor and a turbine according to another embodiment of the present disclosure may suck the air in the hospital room 1 using the compressor 20 to maintain the inner portion of the hospital room 1 in the negative pressure state, and may kill the bacteria or the viruses in the air coming out of the hospital room 1 in the high-temperature and humid environment created by the water spray 13, the compressor 20, and the sterilization chamber 30.

In addition, the compressor 20 uses the power generated by the turbine 40, and is configured so that the heat of the air coming out of the turbine 40 is recovered to a suction side of the compressor 20, such that a compression ratio of the compressor 20 may be decreased, and power consumption may thus be reduced, thereby securing efficiency of the clean negative pressure hospital room system.

Figure 4:
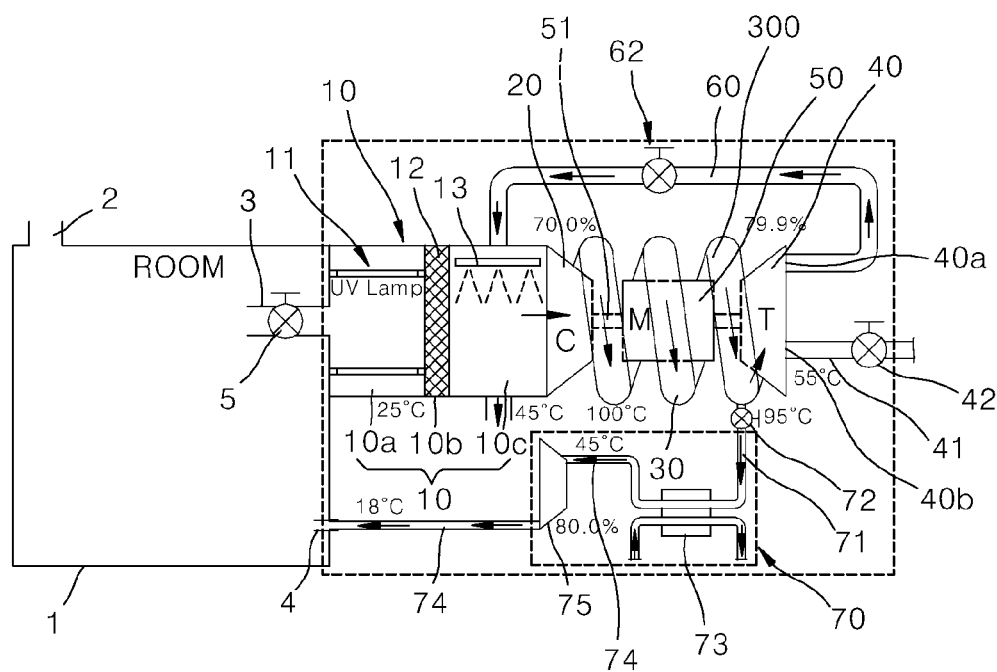
FIG. 4 is a schematic view illustrating a configuration of a clean air conditioning system using a compressor and a turbine according to still another embodiment of the present disclosure.

FIG. 4 is a schematic view illustrating a configuration of a clean air conditioning system using a compressor and a turbine according to still another embodiment of the present disclosure.

Referring to FIG. 4, a clean air conditioning system using a compressor and a turbine according to still another embodiment of the present disclosure is different from the clean air conditioning system using a compressor and a turbine according to another embodiment of the present disclosure described above in that the sterilization chamber 300 is formed as a spiral flow passage, and the other configurations and actions are similar to those of the clean air conditioning system using a compressor and a turbine according to another embodiment of the present disclosure described above. Therefore, a detailed description for the similar configurations will be omitted, and different configurations will be mainly described.

The sterilization chamber 300 is a flow passage formed to connect the compressor 20 and the turbine 40 to each other to allow the air coming out of the compressor 20 to pass therethrough for a minimum set time or more in a high-temperature and humid environment.

The sterilization chamber 300 is formed as the spiral flow passage, such that a time for the air to stay in the high-temperature and humid environment is increased as compared with a straight flow passage, and a sterilization effect may thus be further improved.

The clean air conditioning system using a compressor and a turbine according to the present disclosure may suck the air in the hospital room using the compressor and a turbine to maintain the inner portion of the hospital room in the negative pressure state, and may create the high-temperature and humid environment by the water spray, the compressor, and the sterilization chamber to kill the bacteria or the viruses.

In addition, the compressor accessorily uses the power generated by the turbine, and is configured so that the heat of the air coming out of the compressor is recovered to the suction side of the compressor, such that a compression ratio of the compressor for achieving a desired outlet discharge temperature of the compressor may be decreased, and power consumption may thus be reduced, thereby securing efficiency of the clean air conditioning system.

Further, some of the clean air generated while passing through the sterilization chamber may be directly supplied again to the hospital room through the bypass means.

Furthermore, some of the clean air may be bypassed and utilized for a heater and a cooler, and may thus be used for heating and cooling of the hospital room.

Although the present disclosure has been described with reference to embodiments illustrated in the drawings, it is merely an example, and it will be understood by those skilled in the art that various modifications and equivalent other embodiments are possible from these embodiments. Accordingly, an actual technical protection scope of the present disclosure should be defined by the technical spirit of the claims.

What is claimed is:

1. A clean air conditioning system using a compressor and a turbine, comprising:
   an exhaust chamber exhausting polluted air in a hospital room;
   an ultraviolet lamp provided in the exhaust chamber and sterilizing the air coming out of the hospital room;
   a filter provided in the exhaust chamber and filtering the air passing through the ultraviolet lamp;
   a compressor compressing and discharging the air passing through the filter;
   a sterilization chamber connected to the compressor to form a space in which the air discharged from the compressor is sterilized while passing therethrough;
   a driving turbine driven by the air discharged from the sterilization chamber to generate power and providing the generated power to the compressor; and
   a heat recovery flow passage formed to circulate the air discharged from the compressor to the exhaust chamber through the sterilization chamber and to be connected from the exhaust chamber to the driving turbine.

2. The clean air conditioning system using a compressor and a turbine of claim 1, further comprising a heat recovery valve installed in the heat recovery flow passage and controlling a flow rate of the circulated air.

3. The clean air conditioning system using a compressor and a turbine of claim 1, wherein the sterilization chamber is provided with an ultraviolet lamp.

4. The clean air conditioning system using a compressor and a turbine of claim 1, wherein the sterilization chamber is provided with a filter.

5. The clean air conditioning system using a compressor and a turbine of claim 1, further comprising a heater provided between the sterilization chamber and the hospital room and bypassing some of the air sterilized in the sterilization chamber to supply high-temperature air to the hospital room.

6. The clean air conditioning system using a compressor and a turbine of claim 5, wherein the heater includes:
   a heat exchanger heating external air with high-temperature clean air coming out of the exhaust chamber of the heat recovery flow passage;
   a second clean air supply flow passage bypassing some of the clean air before being introduced into the heat exchanger to supply some of the clean air to the hospital room; and
   a discharge flow passage discharging the clean air from the heat exchanger to the outside.

7. The clean air conditioning system using a compressor and a turbine of claim 1, further comprising an air conditioner driving the driving turbine and bypassing some of discharged clean air to supply low-temperature air to the hospital room.

8. The clean air conditioning system using a compressor and a turbine of claim 7, wherein the air conditioner includes:
- a bypass flow passage bypassing some of the clean air from a turbine discharge flow passage discharging the clean air from the driving turbine to the outside;
- a cooling heat exchanger heat-exchanging the clean air passing through the bypass flow passage with a refrigerant to cool the clean air; and
- a first clean air supply flow passage bypassing some of the clean air before being introduced into the cooling heat exchanger to supply some of the clean air to the hospital room.

* * * * *